United States Patent
Paris et al.

(10) Patent No.: US 6,906,049 B1
(45) Date of Patent: Jun. 14, 2005

(54) CONTRACEPTIVE MEDICINE BASED ON A PROGESTATIONAL AGENT AND AN OESTROGEN AND PREPARATION METHOD

(75) Inventors: Jacques Paris, Nice (FR); Jean Louis Thomas, Charenton le Pont (FR)

(73) Assignee: Laboratoire Theramex (MC)

( * ) Notice: Subject to any disclaimer, the term of this patent is extended or adjusted under 35 U.S.C. 154(b) by 0 days.

(21) Appl. No.: 09/423,108

(22) PCT Filed: Oct. 25, 1999

(86) PCT No.: PCT/FR99/02587

§ 371 (c)(1),
(2), (4) Date: Jun. 12, 2001

(87) PCT Pub. No.: WO01/30355

PCT Pub. Date: May 3, 2001

Related U.S. Application Data

(63) Continuation-in-part of application No. 09/281,147, filed as application No. PCT/FR97/01792 on Oct. 8, 1997.

(30) Foreign Application Priority Data

Oct. 8, 1996 (FR) .............................................. 96 12239
Oct. 25, 1999 (FR) ................................. PCT/FR99/02587

(51) Int. Cl.$^7$ .............................. A61K 31/56; C07J 1/00
(52) U.S. Cl. ........................ 514/170; 514/171; 514/177; 514/178; 514/182; 514/841; 514/843
(58) Field of Search ................................. 514/170, 171, 514/177, 178, 182, 841, 843, 625, 169, 179, 172

(56) References Cited

U.S. PATENT DOCUMENTS 6,500,814 B1 * 12/2002 Hesch ........................ 514/170

FOREIGN PATENT DOCUMENTS

FR 2754179 4/1998

OTHER PUBLICATIONS

Jamin, C. (POPLINE database, abstract of Revue Francaise De Gynecologie Et D Obsterique, 1992, 87(6):370–6).*

* cited by examiner

*Primary Examiner*—Sabiha Qazi
(74) *Attorney, Agent, or Firm*—Dennison, Schultz, Dougherty & MacDonald

(57) ABSTRACT

The present invention relates to the field of chemistry and more particularly to that of therapeutic chemistry.

The invention relates more particularly to novel contraceptive compositions formed from a progestative agent and an oestrogen.

The invention relates specifically to novel pharmaceutical contraceptive compositions, characterized in that they contain, as active ingredients, a nomegestrol ester and oestradiol, in combination or admixture with an inert, non-toxic, pharmaceutically-acceptable vehicle or diluent which is suitable for oral administration.

13 Claims, No Drawings

CONTRACEPTIVE MEDICINE BASED ON A PROGESTATIONAL AGENT AND AN OESTROGEN AND PREPARATION METHOD

PRIOR APPLICATION

The present application is a continuation-in-part of U.S. patent application Ser. No. 09/281,147 filed Mar. 17, 1999 which is a 371 of PCT/FR97/01792 filed Oct. 8, 1997.

Among the contraceptive means most widely and most effectively used, are hormone combinations which act by three different mechanisms, namely, in order of importance:

- inhibition of gonadotropic function, which stops the secretion of FSH and LH from the pituitary and thereby prevents maturation of the ovarian follicles and the occurrence of the ovulatory peak of LH which is essential for oviposition;
- changes in the secretion and the physicochemical properties of the cervical glairy mucus, making it impermeable to spermatozoa;
- inhibition of the development of the uterine mucosa, which becomes unsuitable for egg-implantation.

In the oestro-progestative combinations used hitherto for contraception, the inhibition of gonadotropic function was due mainly to the oestrogenic fraction consisting of a synthetic oestrogen: ethinyloestradiol. By means of the simultaneous use of 19-nor-testosterone derivatives, the progestative fraction reinforces this inhibition of ovulation, and also ensures the peripheral contraceptive effects on the cervical glairy mucus and the endometrium.

However, the use of the oestro-progestative contraceptive combinations currently available has major drawbacks.

Ethinyloestradiol has a very strong impact on liver function; this is reflected essentially by disorders in the synthesis of clotting factors and by abnomalies in the lipid profile of the plasma (Bonnar, et al., 1987; Meade, 1988; Lindberg et al., 1989; von Shoultz et al., 1989; Daly and Bonnar, 1990; Burkman, 1997; Spitzer, 1997). Consequently, the use of oestro-progestative contraceptives is problematic in at-risk women (women suffering from circulatory disorders, women in the perimenopause, women who smoke, etc.). This impact is all the more pronounced since the deleterious effect of ethinyloestradiol can be further increased by the progestative fraction on account of a residual androgenic activity which is often present (Bonnar, 1987; Sabra and Bonnar, 1983; Bonnar et al., 1987).

The progestative fraction of the oestro-progestative contraceptives currently available usually consists of a 19-nor-testosterone derivative which, like ethinyloestradiol, has a negative impact on liver function, the lipid profile and blood vessels. Although this has not been demonstrated definitively, the most modern 19-nor-testosterone derivatives, known as third generation progestatives, are suspected of inducing an increase in thromboembolic accidents (O'Brien, 1999).

To escape the drawbacks of ethinyloestradiol, 19-nor-testosterone derivatives are occasionally used alone in contraception, in two different modes:

- either at low doses, and in this case the contraceptive action is ensured by the peripheral effects of the progestative agent; the reason for this is that the inhibition of ovulation is not constant, since the low doses of progestative agent very often allow the development of ovarian follicles and, in certain cases, an increase in the endogenous secretion of oestradiol;
- or at high doses, so as to unequivocally inhibit ovulation, but at the risk of creating a hypooestrogenia, thus limiting their use in young women.

In summary, it appears to be very useful to have available an oestro-progestative combination which is at least as effective as those currently available, but which is free of their harmful side effects.

To do this, it was easy to do the following:

Replace ethinyloestradiol (EE) with the hormone secreted by the ovaries, 17beta-oestradiol (E2), which is much less toxic than EE (Buckman et al., 1980; Bergink et al., 1981; Lindberg et al., 1989) but is weakly anti-gonadotropic (Hirvonen, 1995). Many attempts have been made, but none has resulted in a product made available to women. In general, the anti-ovulatory effect was clearly obtained, but the many failures were due, in most cases, to poor control of the menstrual cycle with the appearance of spotting and intermenstrual bleeding which made the method unacceptable.

Thus, combinations of natural oestrogens with desogestrel (Wenzl, 1993; Kivinen and Saure, 1996; Csemicsky et al., 1996), with cyproterone acetate (Hirvonen et al., 1988; Hirvonen et al., 1995), with norethisterone (Astedt et al., 1977; World Health Organization, 1980; Serup et al., 1981) were found to be contraceptive, but the intermenstrual bleeding, spotting and poor quality of the periods were unacceptable. For some, the reasons for these failures lay in an insufficient oestrogenic stimulation on account of the poor bioavailability of oestradiol or esters thereof; the excessively intense progestative effect led to a partial inhibition of endometrial proliferation and thus to anarchic bleeding (Hirvonen et al., 1995; Csemicsky et al., 1996). Only one combination gave satisfactory results in terms of controlling the menstrual cycle; this is the combination of oestradiol valerate and dienogest (Oettel et al., 1999; Hoffman et al., 1999). According to these authors, the positive results were thought to be due to a strong dissociation between central activity (anti-ovulatory activity) and peripheral activity (endometrial activity) to the benefit of this latter activity for dienogest. In summary, all of the data published show that the result depends closely on the anti-gonadotropic effect of the progestative agent, the bioavailability of oestradiol or derivatives thereof in the formulation used and an optimum ratio between the oestrogenic and progestative stimulations.

Replace the 19-nor-testosterone derivative with a highly anti-gonadotropic synthetic progestative agent which is known not to have any impact on liver function, sugar-lipid metabolism or clotting factors.

Contraceptive Effect of the Nomegestrol Acetate/Oestradiol Combination

The present invention relates to a novel oral contraceptive formulation for women of child-bearing age (young or perimenopausal); this formulation being based on the combination of:

1. a synthetic progestative agent which is free from any metabolic side effects, nomegestrol or esters thereof, whose anti-gonadotropic effect is found, unexpectedly, to be potentiated by oestradiol or esters thereof;

2. oestradiol, or a derivative thereof (esters or ethers), to compensate for the hypooestrogenia induced by the progestative agent administered over a prolonged period during the cycle;

3. and the use of an optimum weight ratio between the oestrogenic fraction and the progestative fraction, to ensure good control of the menstrual cycle.

The oestrogenic component involves oestradiol or an ester or an ether thereof, such as, for example, the valerate, benzoate, enanthate, etc., the doses used being calculated as oestradiol equivalents. The doses range from 0.3 mg to 3 mg per day with a preference for a range from 0.5 mg to 2 mg per day. According to the literature data (Hirvonen, 1995), a dose of 4 mg is needed to ensure the inhibition of ovulation, but they correspond to the doses used to compensate for hypooestrogenic states. For example, in menopausal women, the dose recommended to compensate for hypooestrogenic states is about 1.5 mg.

The progestative component includes nomegestrol or an ester thereof. Nomegestrol acetate will preferably be used. The range of doses is between 0.1 and 2.5 mg per day and preferably between 0.1 and 1.25 mg per day and more preferably between 0.3 and 1.25 mg/day. At these very low doses, the nomegestrol acetate combined with oestradiol inhibits ovulation and follicle maturation in 100% of cases when the two active principles are administered together from the $1^{st}$ to the $21^{st}$ day of the cycle, with acceptable frequencies of deprivational haemorrhage and intermenstrual bleeding.

The range of the weight ratio of the oestradiol doses to the nomegestrol acetate doses extends from about 0.5 to 5 and this ratio is preferably between about 1 and 3.

The combination of nomegestrol acetate and oestradiol is administered daily, at the same dose, from the $1^{st}$ day of the cycle, for a period which may range from 21 to 28 days. Next, the women receive a placebo tablet daily for the period of time required to complete the 28-day cycle (0 to 7 days).

Nomegestrol acetate is a powerful, orally-active progestative agent which has a novel pharmacological profile:

like 19-nor-testosterone derivatives, nomegestrol acetate bears high anti-gonadotropic activity but, unlike these 19-nor-testosterone derivatives, it does not display any residual androgenic or oestrogenic activity and it has a strong anti-oestrogen activity.

like 17 alpha-hydroxyprogesterone derivatives, it has a pure pharmacological profile, but, unlike the above derivatives, it has a powerful anti-gonadotropic effect.

It belongs to the category of progestative agents known as hybrids (Oettel et al., 1999) which do not bear deleterious metabolic effects on account of the absence of the 17α-ethinyl function, and which combine the advantages of progesterone derivatives with those of the more modern 19-nor-testosterone derivatives.

A clinical trial similar to the Kaufmann's trial, made it possible to show that the endometrial conversion is obtained with a daily dose of 1 mg of nomegestrol acetate, i.e. 10 mg for the entire cycle. It has previously been shown (Bazin et al., 1987) that the inhibition of ovulation and of follicle development were obtained in women with a daily dose of 2.5 mg of nomegestrol acetate. The ratio of the ovulation-inhibiting activity in women (in mg/day) to the endometrial luteinizing ↔tivity (in mg/cycle) as defined by Neumann (1977) is thus in the order of 0.2, i.e. close to those of cyproterone acetate and chlormadinone acetate; this indicates a strong central activity (Oettel et al., 1999). In this sense, it clearly differs from dienogest, whose activity is disequilibrated to the benefit of the peripheral activity. Consequently, the results observed with an oestradiol valerate/dienogest contraceptive combination do not in any way suggest and do not make obvious the results observed with the oestradiol/nomegestrol acetate combination according to the invention.

Study of the anti-ovulatory power of the nomegestrol acetate/oestradiol combination shows an unexpected potentiation of the anti-gonadotropic effects of nomegestrol acetate by oestradiol, since the inhibition of ovulation and of follicle development are obtained with a low dose, in the order of 0.625 mg. This results cannot result from an anti-gonadotropic effect of oestradiol, nor even from an addition of effects between the two active principles since the doses of oestradiol used are very much lower than the doses known to inhibit ovulation (Hirvonen et al., 1995). Consequently, this unexpected observation is a sign of a real innovation, since it allows the use of lower doses of progestative agent and thus better tolerance; it differs from the subject of French Patent 2,754,179 (to the Applicant), in which the range of nomegestrol acetate doses could extend from 1.5 to 5 mg.

The present invention thus relates to an oestro-progestative agent administered in single-stage mode from the $1^{st}$ day of the cycle for 21 to 28 days. It differs from the claims of many patents which describe the combination of oestradiol or of an oestradiol ester administered in multi-stage modes with modified doses of oestrogenic and/or of the progestative agent from one stage to another and, even occasionally, a change of the progestative agent from one stage to another. Mention should be made in this respect, for example, of patents EP 770338, WO 9741868, WO 9909993, WO 9835682, WO U.S. Pat. No. 9,817,288, WO 9602486, WO 9707074, WO 9707083, WO 9707084, WO 9707085, WO 9707089, WO 9712785, WO 9712785, WO 9712786, WO 9712787, WO 9712788, WO 9712789, WO 23228, WO 9741868, WO 9913882, EP 491,438, EP 491,415, WO 9004330, EP 3092263, U.S. Pat. No. 4,628,051, EP 0911029 A2, EP 0770388 A1 and DE 3229612, as well as the publications by Hirvonen et al. (1988, 1995) which describe a two-stage contraceptive method with the oestradiol valerate/cyproterone acetate combination or that by Hoffmann et al. (1988) which describes a two-stage contraceptive method with the oestradiol valerate/dienogest combination.

The present invention includes a method of contraception combining 17β-oestradiol or an ester or ether thereof and nomegestrol or one of the esters thereof, preferably nomegestrol acetate. This method of contraception is novel with respect to the patents and publications devoted to oestro-progestative combinations of oestradiol (or of one of the esters or ethers thereof) and of a progestative agent administered in single-stage mode, since the literature as a whole shows that the overall clinical result is entirely dependent on the nature of the progestative agent used, its pharmacological profile, its effects on the hypothalamo-hypophyseal axis of the "central" power/"peripheral" power ratio and the ratio of oestrogenic and progestative activity.

For these reasons, the single-stage methods of contraception described in some patents, such as, for example, WO 95/17194, WO 99/12531 and EP 0,253,607, and in some publications, such as, for example, those which deal with norethisterone/oestradiol combinations (Astedt et al., 1977; Task force on oral contraception, 1980; Serup et al., 1981), those which deal with desogestrel/oestradiol combinations (Wenzl et al., 1993; Csemicsky et al., 1996) or combinations of dienogest and oestradiol (Hoffmann et al., 1998) cannot be applied to the combination of nomegestrol acetate/oestradiol since they are validated only for the oestrogen and the progestative agent claimed. Added to this is the fact that the potentiation observed between oestradiol and nomegestrol acetate renders any extrapolation of doses from the pharmacological profile unnecessary. Furthermore, nomegestrol acetate is never cited as a progestative agent which can be used. Patents EP 309,263 and WO 90/04330 cited the possibility of using 17alpha-19-nor-progesterone and esters thereof, but it should be pointed out, on the one hand, that nomegestrol acetate is not a 17alpha-19-nor-progesterone ester, and, on the other hand, that 17alpha-19-nor-progesterone esters bear antidiuretic properties which render them unsuitable for use in women (Paris et al., 1987).

A preferred composition will be one which contains 0.312 mg of nomegestrol acetate per 1 mg of oestradiol or 0.625 mg of nomegestrol acetate and 1 mg of oestradiol or 0.625 mg of nomegestrol acetate and 1.5 mg of oestradiol or alternatively 0.625 mg of nomegestrol acetate and 2 mg of oestradiol.

The pharmaceutical compositions according to the invention are those which are suitable for the digestive route, in particular in the form of plain or film-coated tablets, sugar-coated tablets, gelatine capsules, wafer capsules, pills, cachets or powders, which may or may not contain flavourings. They contain a diluent and/or a filling substance and/or a tabletting adjuvant and/or a lubricant and/or a splitting agent. Film-forming agents which may be mentioned are hydroxypropylmethylcellulose (Hypromellose) and cellulose acetophthalate.

Binders which may be used are polyvinylpyrrolidone, carboxymethylcellulose, crosslinked carboxymethylcellulose, microcrystalline cellulose, ethylcellulose, hydroxyethylcellulose or a starch which may or may not have been chemically modified. Filling substances which may be mentioned are calcium carbonate, magnesium carbonate, magnesium phosphate, clays, zeolites, infusorial earth, etc. Tabletting adjuvants which may be mentioned are powdered sugar or lactose. Lubricants which may be mentioned are talc, calcium stearate, magnesium stearate and colloidal silica. Splitting agents which may be mentioned are mannitol, carboxymethylstarch and polyvinylpyrrolidone.

In general, the weight of the compositions according to the invention ranges between 40 and 100 mg and the composition contains from 80 to 99% of diluents and excipients per 1 to 20% of active principles.

Nomegestrol acetate and oestradiol can be administered simultaneously, combined in a single formulation, or, on the contrary, may be present in two pharmaceutical forms to be ingested successively or simultaneously.

The daily dosage will be 1 or 2 intakes and the duration of the treatment will be exerted throughout the entire month. In total, the mean monthly dose of nomegestrol acetate will range from 8 mg to 75 mg. The doses are fully tolerated.

EXAMPLE I

Examples of Formulations

The combination of nomegestrol acetate and oestradiol is presented in the form of plain or film-coated tablets.

In these compositions, oestradiol is advantageously introduced into the final mixture in the form of a premix containing from 2 to 5% of oestradiol in povidone (10 to 25%) and lactose (qs 100%), such as, for example:

| FORMULATIONS | IN MG/1 TABLET | IN % |
| --- | --- | --- |
| Oestradiol | 1.00 | 2.50 |
| Povidone | 6.00 | 15.00 |
| Lactose | 33.00 | 82.50 |
| Isopropyl alcohol | # 6.14 | # 15.35 |
| Demineralized water | # 1.06 | # 2.67 |
| TOTAL ON DRY | 40.00 | 100.00 |

This premix is introduced into the final mixture in order to obtain a tablet by direct tabletting.

The plain finished tablets generally weigh from 60 to 90 mg and have the overall formulation below:

| FORMULATIONS OF THE PLAIN TABLETS Composition | |
| --- | --- |
| | in mg/tablet |
| Oestradiol premix qs | 0.5 to 1.5 |
| Nomegestrol acetate | 0.300 to 2.500 |
| Colloidal silica | 0.300 to 1.500 |
| Crospovidone | 2.500 to 5.000 |
| Lactose | 4.000 to 40.000 |
| Cellulose | 6.000 to 40.000 |
| Stearic acid | 0.900 to 3.00 |
| Talc | 0.450 to 1.500 mg |

By way of example, mention may be made of tablets weighing 90 mg and having the formulation below:

| Examples of formulations (UF = unit formulation) 90 mg tablets | | |
| --- | --- | --- |
| FORMULATIONS | UF mg/1 90 mg tablet | UF % |
| Premix containing 2.5% oestradiol | 40.000 | 44.45 |
| Nomegestrol acetate | 0.300 | 0.33 |
| Colloidal silica (Aerosil 200) | 0.495 | 0.55 |
| Crospovidone (Polyplasdone XL) | 3.240 | 3.60 |
| Lactose | 26.000 | 28.89 |
| Microcrystalline cellulose (Avicel PH 101) | 17.265 | 19.18 |
| Stearic acid AC68/50VG | 1.800 | 2.00 |
| Talc | 0.900 | 1.00 |
| TOTAL | 90.000 | 100.00 |
| Premix containing 2.5% oestradiol | 40.000 | 44.45 |
| Nomegestrol acetate | 2.500 | 2.77 |
| Colloidal silica (Aerosil 200) | 0.495 | 0.55 |
| Crospovidone (Polyplasdone XL) | 3.240 | 3.60 |
| Lactose | 24.900 | 27.67 |
| Microcrystalline cellulose (Avicel PH 101) | 16.165 | 17.96 |
| Stearic acid AC68/50VG | 1.800 | 2.00 |
| Talc | 0.900 | 1.00 |
| TOTAL | 90.000 | 100.00 |
| Premix containing 2.5% oestradiol | 60.000 | 66.67 |
| Nomegestrol acetate | 0.300 | 2.77 |
| Colloidal silica (Aerosil 200) | 0.495 | 0.55 |
| Crospovidone (Polyplasdone XL) | 3.240 | 3.60 |
| Lactose | 12.215 | 8.91 |
| Microcrystalline cellulose (Avicel PH 101) | 13.050 | 14.50 |

-continued

Examples of formulations (UF = unit formulation) 90 mg tablets

| FORMULATIONS | UF mg/1 90 mg tablet | UF % |
|---|---|---|
| Stearic acid AC68/50VG | 1.800 | 2.00 |
| Talc | 0.900 | 1.00 |
| TOTAL | 90.000 | 100.00 |
| Premix containing 2.5% oestradiol | 60.000 | 66.67 |
| Nomegeatrol acetate | 0.625 | 0.69 |
| Kollidon 25 | 9.000 | 10.00 |
| Colloidal silica (Aerosil 200) | 0.495 | 0.55 |
| Crospovidone (Polyplasdone XL) | 3.240 | 3.60 |
| Microcrystalline cellulose (Avicel PH 101) | 13.050 | 14.50 |
| Stearic acid AC68/50VG | 1.800 | 2.00 |
| Talc | 0.900 | 1.00 |
| Lactose | 0.890 | 0.99 |
| TOTAL | 90.000 | 100.00 |

Plain tablets weighing 60 mg and having the formula below, can also be prepared:

Examples of formulations (UF = unit formulation) 60 mg tablets

| FORMULATIONS | UF mg/1 60 mg tablet | UF % |
|---|---|---|
| Premix containing 4.0% oestradiol | 25.000 | 41.67 |
| Nomegestrol acetate | 0.300 | 0.50 |
| Colloidal silica (Aerosil 200) | 0.324 | 0.54 |
| Crospovidone (Polyplasdone XL) | 3.000 | 5.00 |
| Lactose | 16.076 | 26.779 |
| Microcrystalline cellulose (Avicel PH 101) | 13.500 | 22.50 |
| Stearic acid AC68/50VG | 1.200 | 2.00 |
| Talc | 0.600 | 1.00 |
| TOTAL | 60.000 | 100.00 |
| Premix containing 4.0% oestradiol | 25.000 | 41.67 |
| Nomegestrol acetate | 2.5000 | 4.17 |
| Colloidal silica (Aerosil 200) | 0.324 | 0.54 |
| Crospovidone (Polyplasdone XL) | 3.000 | 5.00 |
| Lactose | 14.976 | 24.96 |
| Microcrystalline cellulose (Avicel PH 101) | 12.400 | 20.66 |
| Stearic acid AC68/50VG | 1.200 | 2.00 |
| Talc | 0.600 | 1.00 |
| TOTAL | 60.000 | 100.00 |
| Premix containing 4.0% oeatradiol | 37.500 | 62.50 |
| Nomegestrol acetate | 0.625 | 1.04 |
| Kollidon 25 | 7.000 | 11.67 |
| Colloidal silica (Aerosil 200) | 0.324 | 0.54 |
| Crospovidone (Polyplasdone XL) | 3.000 | 5.00 |
| Microcrystalline cellulose (Avicel PH 101) | 8.213 | 13.69 |
| Stearic acid AC68/50VG | 1.200 | 2.00 |
| Talc | 0.600 | 1.00 |
| Lactose | 1.538 | 2.56 |
| TOTAL | 60.000 | 100.00 |
| Premix containing 4.0% oestradiol | 37.500 | 62.50 |
| Nomegestrol acetate | 0.300 | 4.17 |
| Colloidal silica (Aerosil 200) | 0.324 | 0.54 |

Examples of formulations (UF = unit formulation) 60 mg tablets

| FORMULATIONS | UF mg/1 60 mg tablet | UF % |
|---|---|---|
| Crospovidone (Polyplasdone XL) | 3.000 | 5.00 |
| Lactose | 7.076 | 16.08 |
| Microcrystalline cellulose (Avicel PH 101) | 10.000 | 8.71 |
| Stearic acid AC68/50VG | 1.200 | 2.00 |
| Talc | 0.600 | 1.00 |
| TOTAL | 60.000 | 100.00 |
| Premix containing 4.0% oestradiol | 25.000 | 41.67 |
| Nomegestrol acetate | 2.500 | 4.17 |
| Colloidal silica (Aerosil 200) | 0.324 | 0.54 |
| Crospovidone (Polyplasdone XL) | 3.000 | 5.00 |
| Lactose | 14.976 | 24.96 |
| Microcrystallne cellulose (Avicel PH 101) | 12.400 | 20.66 |
| Stearic acid AC68/50VG | 1.200 | 2.00 |
| Talc | 0.600 | 1.00 |
| TOTAL | 60.000 | 100.00 |

These tablets can be film-coated with, for example:
film-forming agents based on polyvinyl alcohol, of the type OPADRY PVA "moisture barrier" (polyvinyl alcohol, titanium dioxide, purified talc, lecithin, xanthan gum, pigments, lacquers), or
film-forming agents based on cellulose, of the type SEPIFILM L.P. [HPMC (hydroxypropylmethyl cellulose)], microcrystalline cellulose, stearic acid, pigments, lacquers.

EXAMPLE II

Potentiation of the Anti-gonadotropic Effect of Nomegestrol Acetate with Oestradiol The anti-ovulatory action of the oestradiol/nomegestrol acetate combination was evaluated in a randomized double-blind study on 38 female volunteers, in good health, aged 18 to 35, in the period of ovarian activity, for whom it was checked beforehand, by means of an assay of the progesterone in the plasma and the establishment of a temperature curve, that they had ovulatory menstrual cycles.

The women were monitored for two consecutive cycles: the first was a control cycle without treatment; during the following cycle (cycle under treatment), they received a hormonal treatment administered orally daily from the $1^{st}$ to the $21^{st}$ day of the cycle.

According to the randomization:

9 women received 1.5 mg of oestradiol+0.625 mg of nomegestrol acetate (group A), 10 others received 1.5 mg of oestradiol+1.25 mg of nomegestrol acetate (group B), another 10 received 1.5 mg of oestradiol+2.5 mg of nomegestrol acetate (group C), and the other 9 were treated with nomegestrol acetate alone at a dose of.2.5 mg (group D).

During the control cycle, the hormonal parameters were not significantively different among the four groups. Table I indicates the mean concentrations observed for each hormonal parameter in the course of the 21 days of treatment.

In all the women, and irrespective of the doses administered, the cycles under treatment were all anovulatory, with a disappearance of the mid-cycle peak of LH and a progesterone level in the plasma of less than 1 ng/ml.

Comparison of the hormonal parameters in groups C and D made it possible to show that the combination of oestradiol with nomegestrol acetate not only significantly increased the oestradiol level in the plasma, but also reinforced the anti-gonadotropic effect of the progestative agent. Specifically, in the presence of oestradiol, the LH and FSH levels were found to be statistically lower than those observed when nomegestrol acetate was administered alone.

combination on the cycle. In all of the women treated with the oestro-progestative combination, it was thus observed that the duration of the cycle did not exceed 1 month in 50% of cases, that spotting was totally absent from one woman in two and that the deprivational haemorrhage after stopping the treatment was on average 5.4 days and did not exceed 7 days in 86% of the women. These data did not differ among the groups. As regards the first treatment cycle, they reflect a satisfactory level of tolerance; in point of fact, it is known that the quality of the cycles obtained with this type of combination improves after a few cycles of treatment.

TABLE I

Mean concentrations in the plasma (m ± sem) of gonadotrophins (LH and FSH) and of ovarian steroids (oestradiol and progesterone) in the course of a cycle under treatment with 3 oestradiol/nomegestrol acetate (E2/NOMAC) combinations. Comparison with the treatment with nomegestrol acetate alone

| Hormonal Parameter | Group A (n = 9) 1.5 mg E2 + 0.625 mg NOMAC | Group B (n = 10) 1.5 mg E2 + 1.25 mg NOMAC | Group C (n = 10) 1.5 mg E2 + 2.5 mg NOMAC | Group D (n = 9) 2.5 mg NOMAC | p (ANOVA) Comparison A, B, C | p (ANOVA) Comparison C and D |
|---|---|---|---|---|---|---|
| LH (mIU/ml) | 4.1 ± 0.51 | 3.0 ± 0.51 | 2.7 ± 0.49 | 5.6 ± 0.62 | 0.135 | 0.002 |
| FSH (mIU/ml) | 6.2 ± 0.42 | 6.6 ± 0.52 | 5.4 ± 0.75 | 7.6 ± 0.28 | 0.318 | 0.019 |
| Progesterone ng/ml | 0.11 ± 0.031 | 0.07 ± 0.024 | 0.03 ± 0.009 | 0.07 ± 0.014 | 0.068 | 0.056 |
| Oestradiol pg/ml | 62.0 ± 7.90 | 57.6 ± 4.53 | 47.2 ± 5.61 | 31.9 ± 3.91 | 0.225 | 0.043 |

When nomegestrol acetate is combined with oestradiol, it exerts anti-gonadotropic effects, even at low doses (0.625 and 1.25 mg), since the hormonal parameters were not found to be significantively different in groups A, B and C.

This synergistic effect of oestradiol is confirmed by comparing the results of this study with those of another clinical trial performed according to the same methodology, but with the progestative agent alone. This comparison in fact shows that, at a dose of 1.25 mg of nomegestrol acetate, the addition of oestradiol has no appreciable influence on the levels of progesterone and of gonadotrophins (LH and FSH) in the plasma. On the other hand, the addition of oestradiol lowers the plasmatic levels of oestradiol, assayed 24 hours after taking the medicinal product, by about 300%; this parameter is a good reflection of the endogenous secretion of the ovaries (Table II).

It is known that nomegestrol acetate given alone at a rate of 1.25 mg per day abolishes ovulation and prevents the formation of the corpus luteum, while at the same time resulting in an increase in the level of oestradiol in the plasma, which is evidence of follicle development without ovulation, as is encountered with the progestative micropill.

This study has thus shown that the addition of a dose of oestradiol, which is insufficient to block ovulation by itself, reinforces the anti-ovulatory effects of the progestative agent and also inhibits folliculogenesis, and maintains oestradiol levels markedly below 100 pg/ml an appreciable time after taking the medicinal product. It is thus possible to observe anti-ovulatory effects with lower doses of nomegestrol acetate than those initially used when it is combined with oestradiol; this confirms, in the new study, the results obtained with 0.625 mg of nomegestrol acetate (NOMAC) per day, combined with oestradiol.

In this study, the reading of the genital bleeding allows to evaluate the effect of the oestradiol/nomegestrol acetate

TABLE II

Mean concentrations (m ± sem) of gonadotropins (LH and FSH) and of oestradiol in the plasma vith 1.25 mg of nomegestrol acetate combined or not combined with oestradiol.

| Hormonal Parameter | Cycle | NOMAC 1.25 mg (n = 3)[1] | NOMAC 1.25 + E2 1.5 mg (n = 10)[2] |
|---|---|---|---|
| LH (mIU/ml) | Control | 4.5 (4.0–5.0) | 7.1 ± 0.82 |
| | Treated | 3.1 (2.6–3.7) | 3.0 ± 0.51 |
| FSH (mIU/ml) | Control | 4.3 (4.0–4.5) | 6.6 ± 0.28 |
| | Treated | 3.3 (2.5–4.2) | 6.9 ± 0.48 |
| Oestradiol pg/ml | Control | 112.0 (64.8–203.8) | 132.9 ± 10.57 |
| | Treated | 158.8 (99.5–201.7) | 47.2 ± 5.61 |

E2 = oestradiol; NOMAC = nomegestrol acetate
[1] = m (breadth);
[2] = m ± sem

EXAMPLE III

Effect of the Nomegestrol Acetate/Oestradiol Combination on the Endometrium

A study was carried out to test the effects on the endometrium of several doses of nomegestrol acetate combined with an oral dose of oestradiol equivalent to 1.5 mg.

In the course of this study, 179 women who had been menopausal for at least 3 years received continuously every day 2 mg of oestradiol valerate combined with four different doses of nomegestrol acetate: 5 mg (n=47), 2.5 mg (n=42), 1.25 mg (n=43) and 0.625 mg (n=47).

The effect of these four combinations on the endometrium was evaluated by measuring the thickness of the endometrium by endovaginal echography and by carrying out a biopsy on the endometrium before and after the treatment.

Table IV indicates the results of the echographic examination. At the end of the treatment, the mean thickness of the endometrium remains less than or in the order of 4 mm. The increase in thickness under treatment is 0.39 mm on average with the lowest dose of nomegestrol acetate (0.625 mg/day). It increases slightly as the dose increases, but remains less than 1.5 mm with 2.5 mg/day.

The biopsies examined at the end of the study (Table V) revealed no proliferative or hyperplasic appearance of the uterine mucosa after 6 months of treatment. The greatest number of atrophic endometria were observed with the lowest doses of nomegestrol acetate.

These results indicate that low doses of nomegestrol acetate administered continuously with oestradiol are capable of sufficiently impregnating the endometrium and of ultimately preventing the growth of the uterine mucosa.

TABLE III

Endometrial thickness after 6 months of treatment with several continuous combined combinations based on oestradiol (2 mg of oestradiol valerate) and nomegeatrol acetate (NOMAC) at several doses

| Doses of NOMAC (mg/day) | 0.625 (n = 35) | 1.25 (n = 33) | 2.5 (n = 34) | 5 (n = 41) |
|---|---|---|---|---|
| Mean thickness at the end of treatment (mm) | 3.18 (1.65) | 4.05 (3.75) | 3.93 (2.10) | 3.83 (2.72) |
| Mean increase in thickness under treatment (mm) | 0.39 (1.67) | 1.12 (3.67) | 1.36 (1.54) | 1.57 (2.39) |

( ) = standard deviation

TABLE IV

Histological appearance of the endometrium after 6 months of treatment with several continuous combined combinations based on oestradiol (2 mg of oestradiol valerate) and nomegestrol acetate (NOMAC) at several doses

| Doses of NOMAC (mg/day) | 0.625 (n = 32) | 1.25 (n = 33) | 2.5 (n = 34) | 5 (n = 40) |
|---|---|---|---|---|
| Absence of endometrium | 5 (15.6) | 10 (30.3) | 3 (8.8) | 3 (7.5) |
| Atrophic endometrium | 19 (59.4) | 10 (30.3) | 8 (23.5) | 3 (7.5) |
| Secretory endometrium | 8 (25.0) | 12 (36.4) | 22 (64.7) | 34 (85.0) |

TABLE IV-continued

Histological appearance of the endometrium after 6 months of treatment with several continuous combined combinations based on oestradiol (2 mg of oestradiol valerate) and nomegestrol acetate (NOMAC) at several doses

| Doses of NOMAC (mg/day) | 0.625 (n = 32) | 1.25 (n = 33) | 2.5 (n = 34) | 5 (n = 40) |
|---|---|---|---|---|
| Polyp | 0 | 1 (3.0) | 1 (2.9) | 0 |

( ) = percentage
No endometrium was proliferative or hyperplasic

What is claimed is:

1. A method of achieving contraception in a female human comprising orally administering to said female a composition comprising estradiol or an ester or ether thereof, and 0.1 to 2.5 mg of nomegestrol, acetate, in a weight ratio of estadiol fraction to nomegestrol acetate of 0.5 to 5, from the beginning of their menstrual cycles for 21 up to 28 days and administering a placebo for the balance of the menstrual cycle.

2. The method of claim 1, wherein the weight ratio is 1 to 3.

3. The method of claim 1 wherein the contraceptive formulation is in the form of tablets, plain tablets, film coated tablets, sugar-coated tablets, soft gelatine capsules, pills, cachets or powders.

4. The method of claim 1, the dose of nomegestrol as an acetate is 0.1 mg to 2.5 mg per unit dosage.

5. The method of claim 1, comprising the dose of nomegestrol as an acetate is 0.3 to 1.25 mg per unit dosage.

6. The method of claim 1, wherein the dose of estradiol or of one of the esters or ethers is 0.3 to 3 mg expressed as estradiol.

7. The method of claim 1, wherein the dose of estradiol or its esters is 0.5 mg to 2 mg, expressed as estradiol.

8. The method of claim 1, comprising a combination of 0.625 mg of nomegestrol acetate and 0.5 mg of estradiol.

9. The method of claim 1, comprising a combination of 0.625 mg of nomegestrol acetate and 1 mg of estradiol.

10. The method of claim 1, comprising a combination of 0.625 mg of nomegestrol acetate and 1.5 mg of estradiol.

11. The method of claim 1, comprising a combination of 0.625 mg of nomegestrol acetate and 2 mg of estradiol.

12. The method of claim 1, comprising a combination of 0.3 mg of nomegestrol acetate and 1 mg of estradiol.

13. The method of claim 1, comprising a combination of 0.3 mg of nomegestrol acetate and 1.5 mg of estradiol.

* * * * *

UNITED STATES PATENT AND TRADEMARK OFFICE
CERTIFICATE OF CORRECTION

PATENT NO.    : 6,906,049 B1
DATED         : June 14, 2005
INVENTOR(S)   : Jacques Paris et al.

It is certified that error appears in the above-identified patent and that said Letters Patent is hereby corrected as shown below:

Title page,
Item [22], should read as follows:
-- Filed:   October 29, 1999 --.
Delete Items [86], [87] and [63].
Item [30], Foreign Application Priority Data, should read
-- Oct. 25, 1999 (WO) PCT/FR99/02587 --.

Column 1,
Delete lines 4 through 7.

Signed and Sealed this

Twenty-third Day of August, 2005

JON W. DUDAS
*Director of the United States Patent and Trademark Office*